(12) United States Patent
Ban et al.

(10) Patent No.: US 11,576,657 B2
(45) Date of Patent: Feb. 14, 2023

(54) ULTRASOUND DIAGNOSIS APPARATUS FOR CONTROLLING VOLUME OF DOPPLER SOUND AND METHOD OF CONTROLLING THE SAME

(71) Applicant: SAMSUNG MEDISON CO., LTD., Gangwon-do (KR)

(72) Inventors: Dahee Ban, Seoul (KR); Sung-Ah Park, Seoul (KR); Ra-Young Yoon, Seoul (KR); Jaesung Lee, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 37 days.

(21) Appl. No.: 17/174,700

(22) Filed: Feb. 12, 2021

(65) Prior Publication Data
US 2021/0275150 A1 Sep. 9, 2021

(30) Foreign Application Priority Data
Mar. 6, 2020 (KR) .................. 10-2020-0028248

(51) Int. Cl.
*A61B 8/00* (2006.01)
*A61B 8/08* (2006.01)

(52) U.S. Cl.
CPC .............. *A61B 8/54* (2013.01); *A61B 8/461* (2013.01); *A61B 8/488* (2013.01); *A61B 8/5207* (2013.01)

(58) Field of Classification Search
CPC ..... A61B 8/488; A61B 8/0891; A61B 8/0866; A61B 8/06; A61B 8/54
See application file for complete search history.

(56) References Cited

U.S. PATENT DOCUMENTS

| | | | |
|---|---|---|---|
| 5,088,497 A | 2/1992 | Ikeda | |
| 5,640,960 A | 6/1997 | Jones et al. | |
| 6,210,168 B1* | 4/2001 | Aiger | G01S 15/8984 434/262 |
| 6,733,454 B1* | 5/2004 | Bakircioglu | G01S 7/5205 600/453 |
| 8,062,223 B2 | 11/2011 | Zwirn et al. | |

(Continued)

FOREIGN PATENT DOCUMENTS

| | | |
|---|---|---|
| JP | H06-017710 U | 3/1994 |
| JP | H09192133 A * | 7/1997 |

(Continued)

OTHER PUBLICATIONS

JP-4497611-B2 (Year: 2010).*

(Continued)

*Primary Examiner* — Joel Lamprecht
*Assistant Examiner* — Nyrobi Celestine
(74) *Attorney, Agent, or Firm* — Morgan, Lewis & Bockius LLP

(57) ABSTRACT

Provided is an ultrasound diagnosis apparatus including an image processor configured to generates an ultrasound image on the basis of an ultrasound signal, an image outputter configured to display the ultrasound image generated by the image processor on the basis of a plurality of parameters, a sound outputter configured to output Doppler sound of the ultrasound image, and a controller configured to control a volume of the Doppler sound on the basis of at least one of the plurality of parameters.

12 Claims, 13 Drawing Sheets

(56) References Cited

U.S. PATENT DOCUMENTS

| | | | |
|---|---|---|---|
| 2003/0100833 A1* | 5/2003 | He | G01S 7/52082 600/453 |
| 2011/0172540 A1 | 7/2011 | Jackson | |
| 2017/0307742 A1 | 10/2017 | Hope Simpson et al. | |
| 2019/0313999 A1 | 10/2019 | Kim | |
| 2019/0388056 A1 | 12/2019 | Rodriquez | |

FOREIGN PATENT DOCUMENTS

| | | |
|---|---|---|
| JP | 2001-008958 A | 1/2001 |
| JP | 2008-036095 A | 2/2008 |
| JP | 4497611 B2 * | 7/2010 |

OTHER PUBLICATIONS

JP-H09192133-A (Year: 1997).*
Extended European Search Report dated Jul. 5, 2021 issued in European Patent Application No. 21157899.2.

* cited by examiner

[FIG. 1]
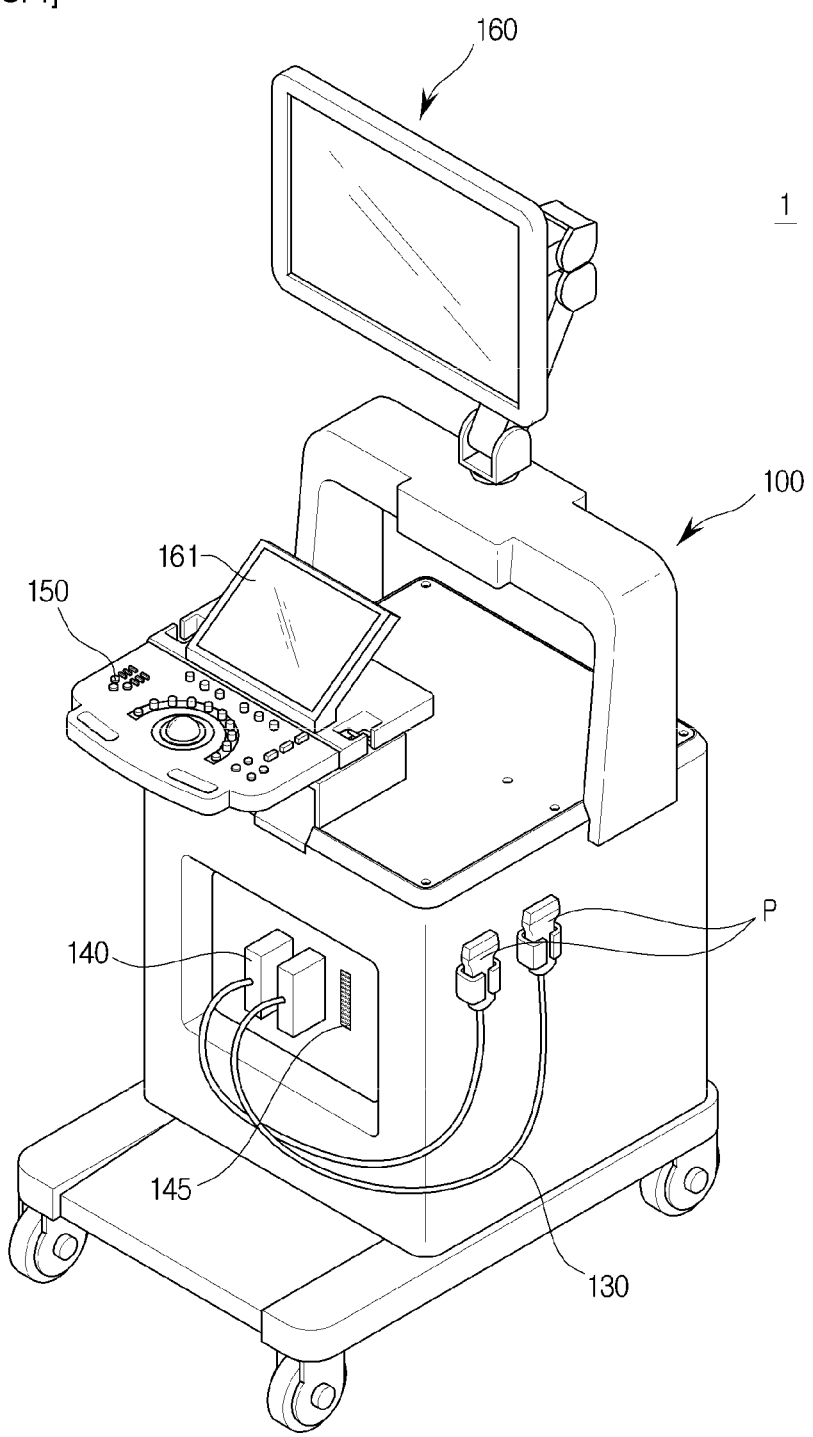

[FIG. 2]
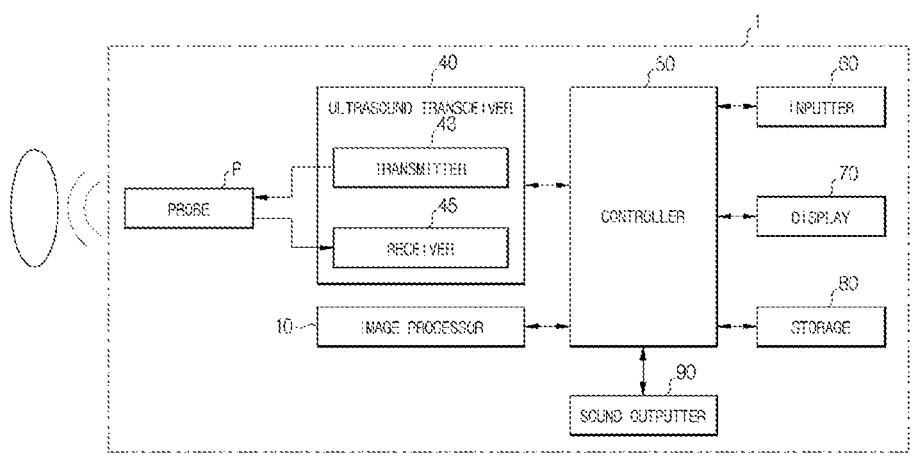

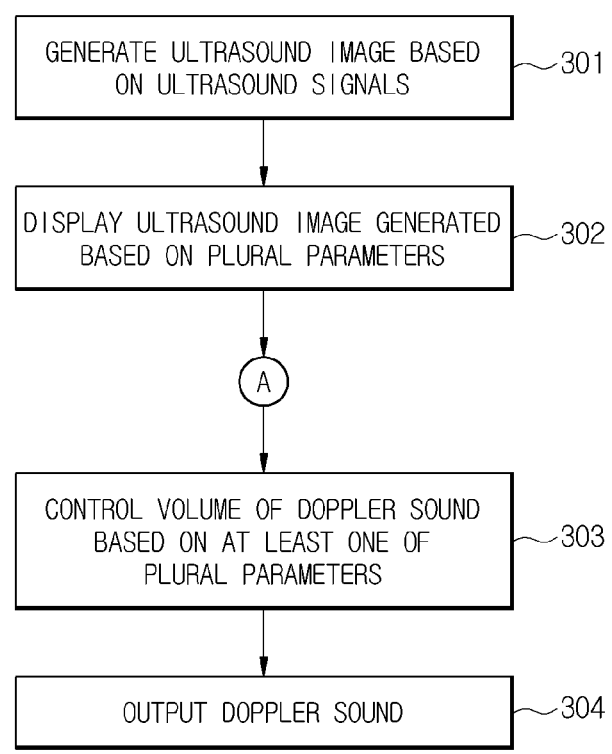

[FIG. 4]
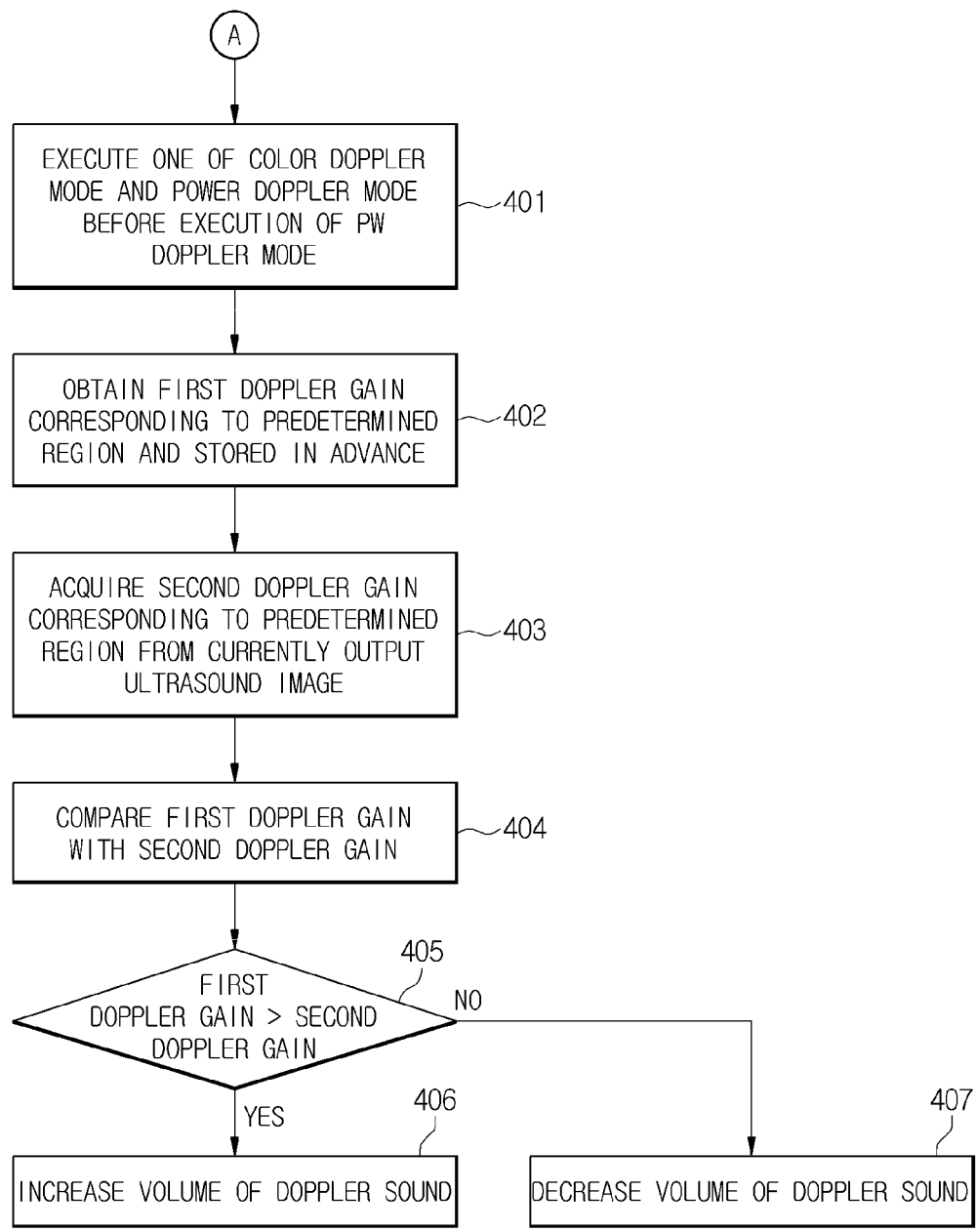

[FIG. 5]
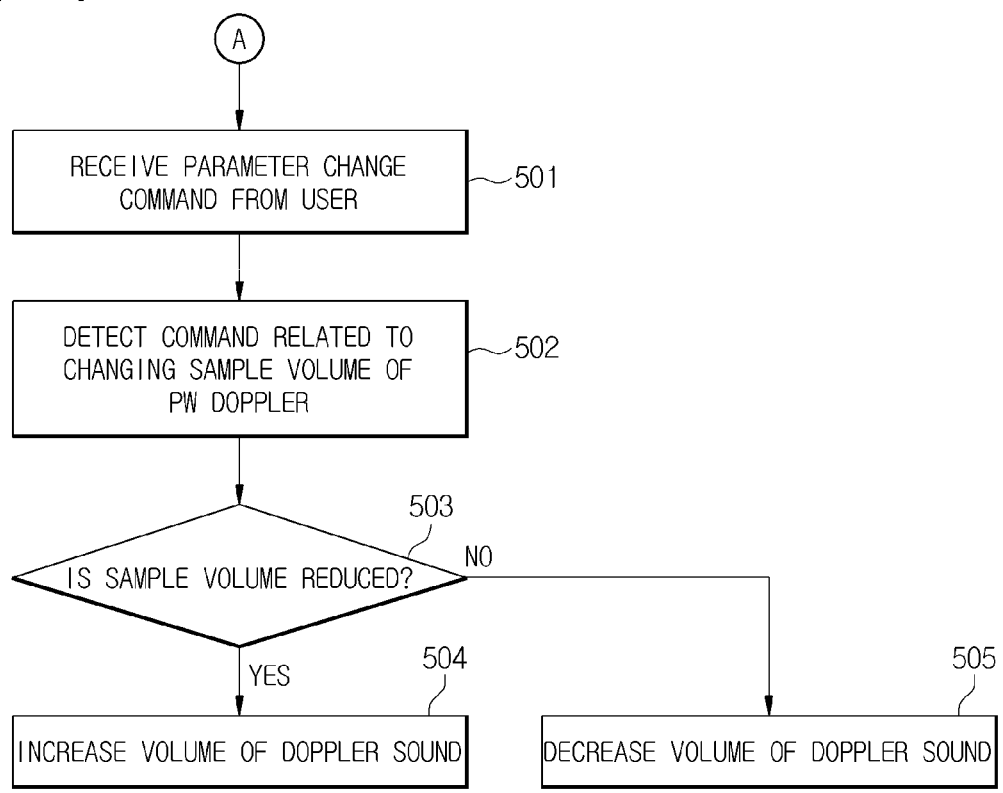

[FIG. 6]
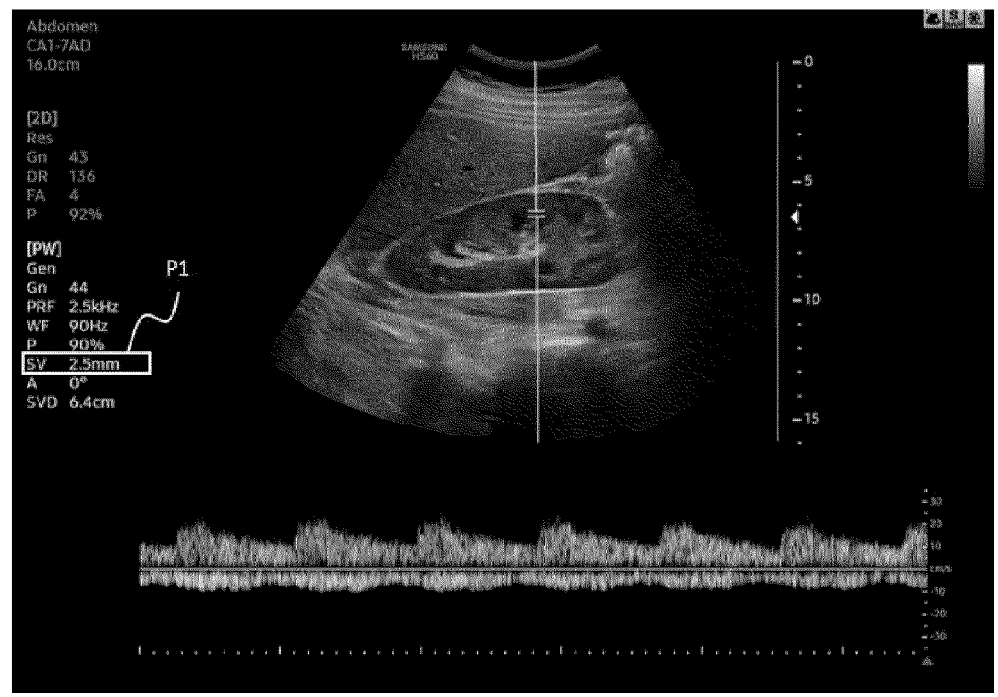

[FIG. 7]
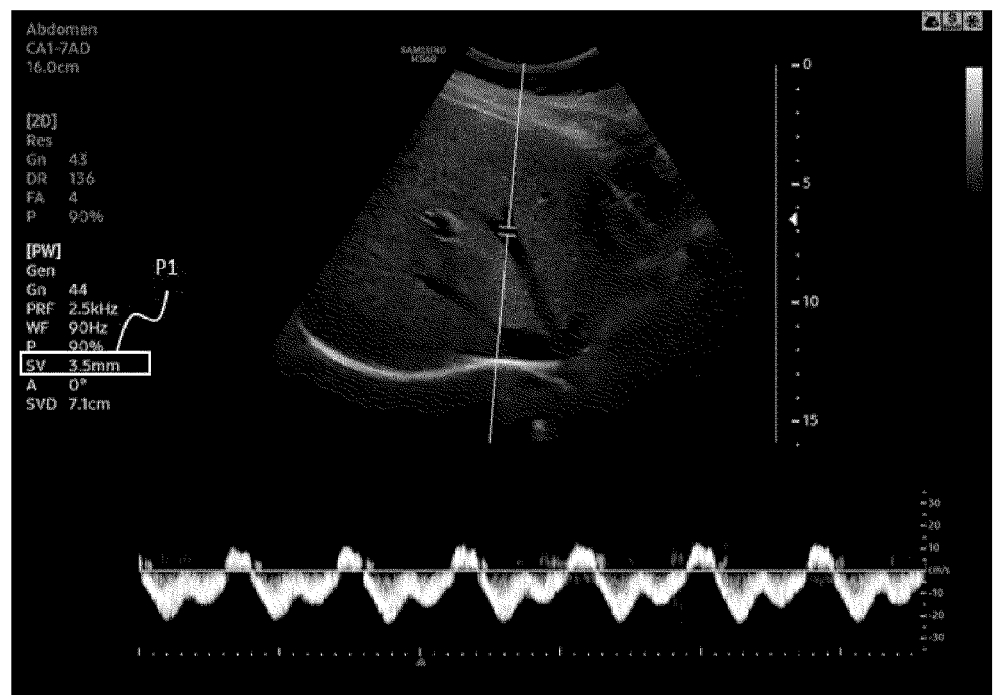

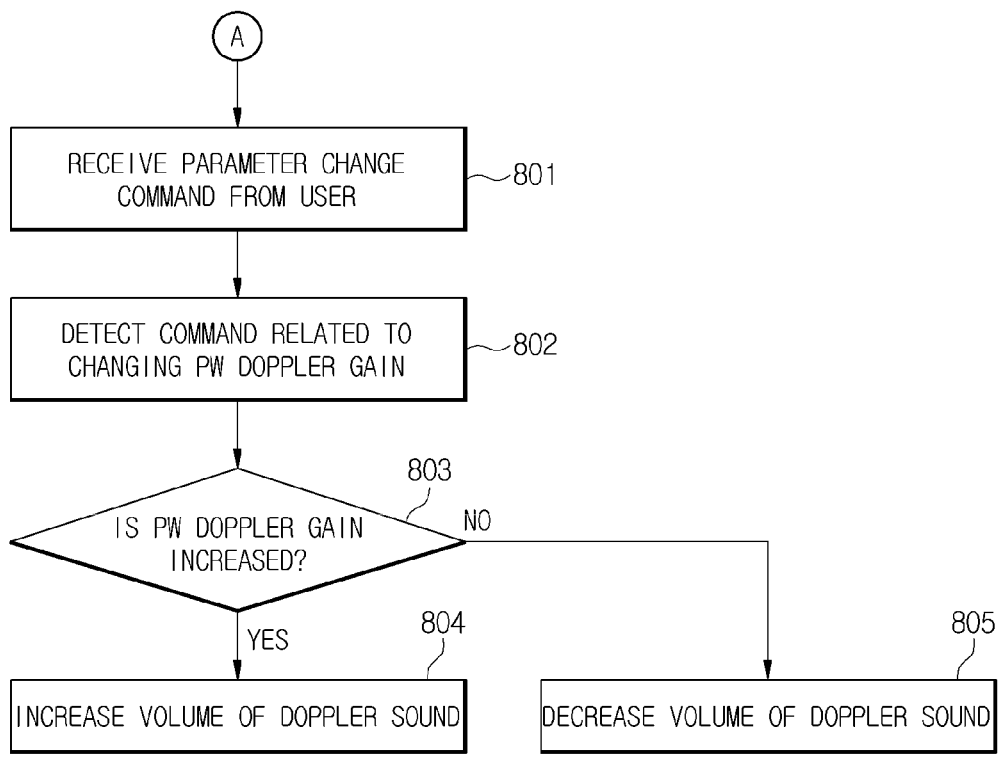

[FIG. 9]
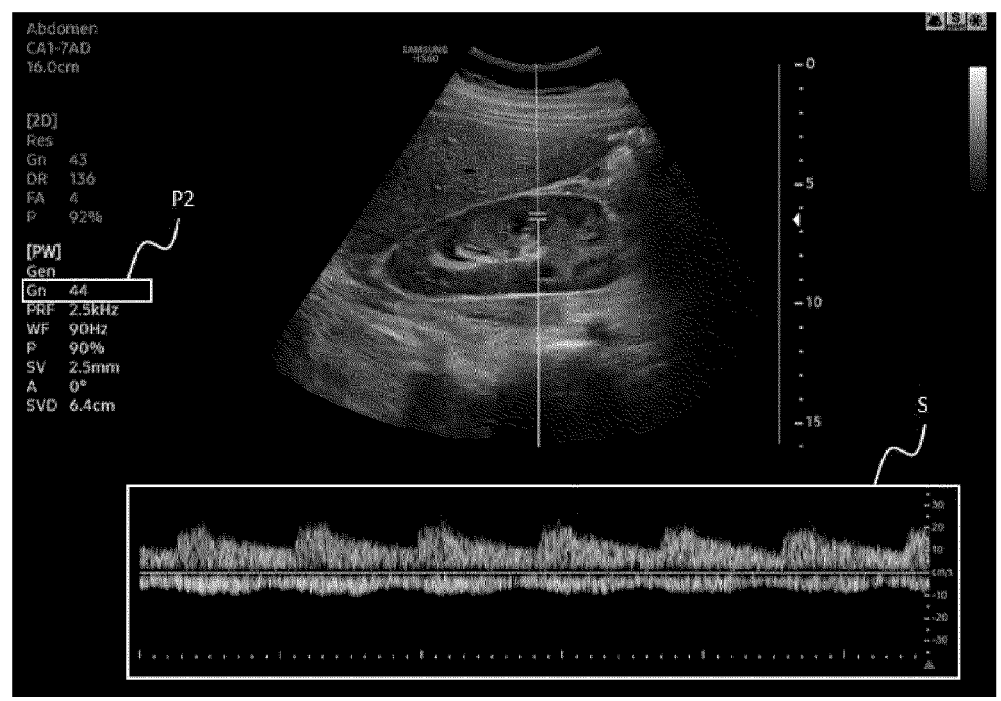

[FIG. 10]
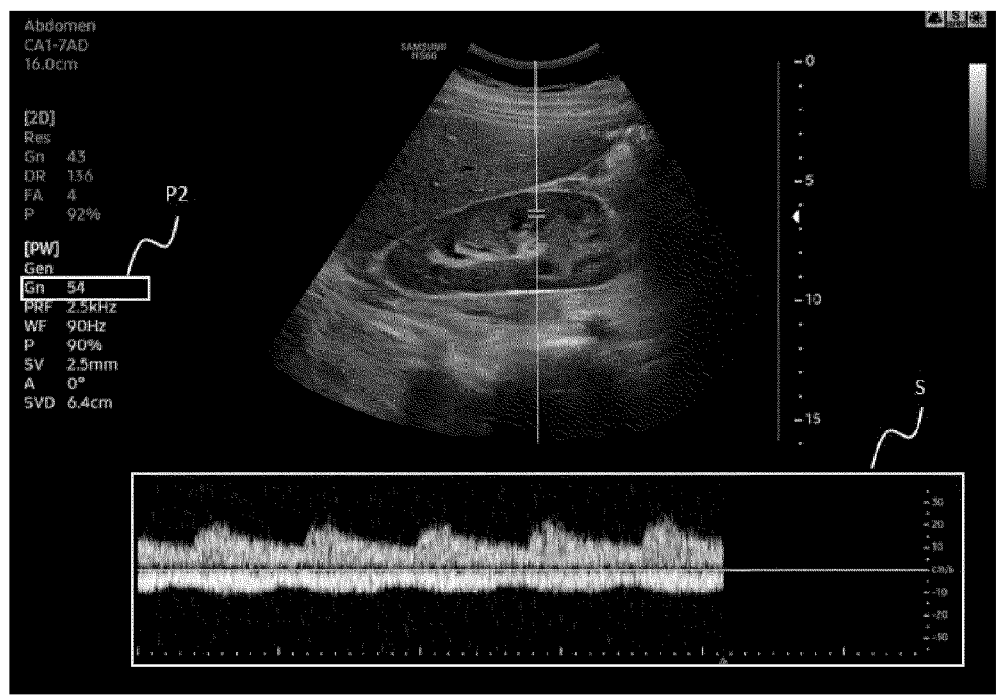

[FIG. 11]
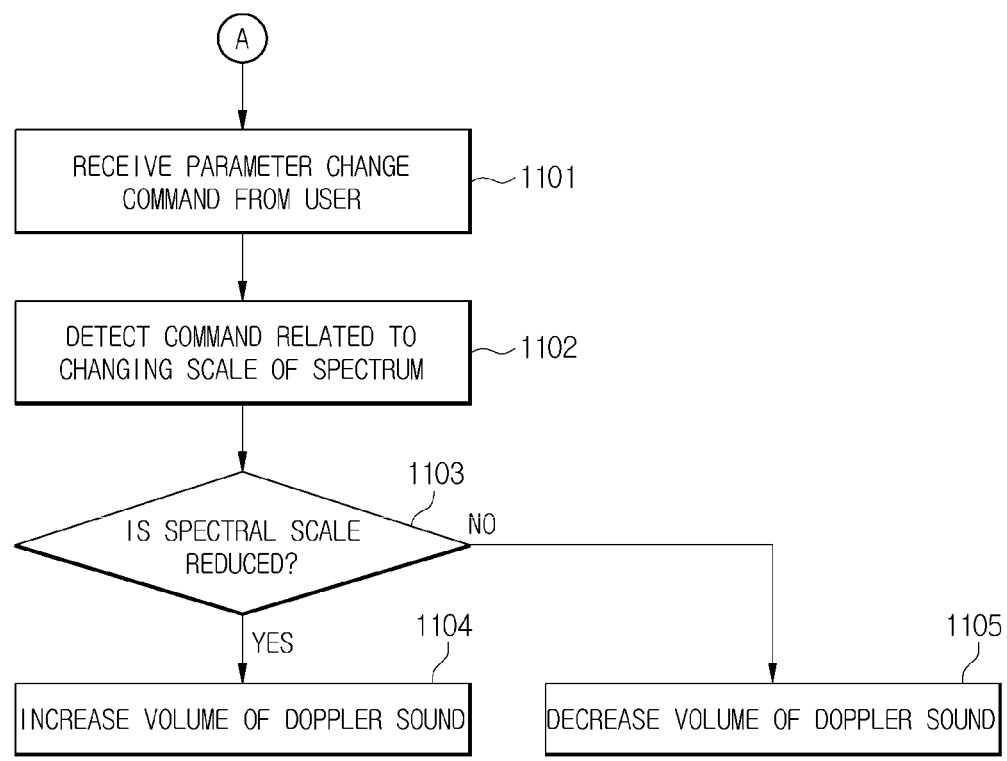

[FIG. 12]
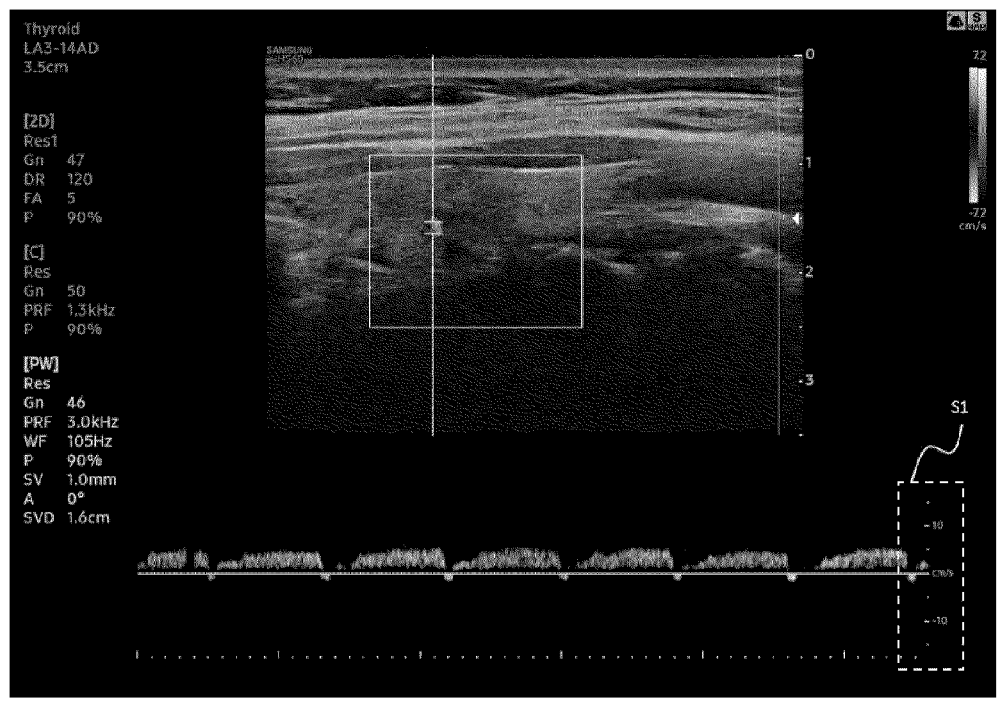

[FIG. 13]
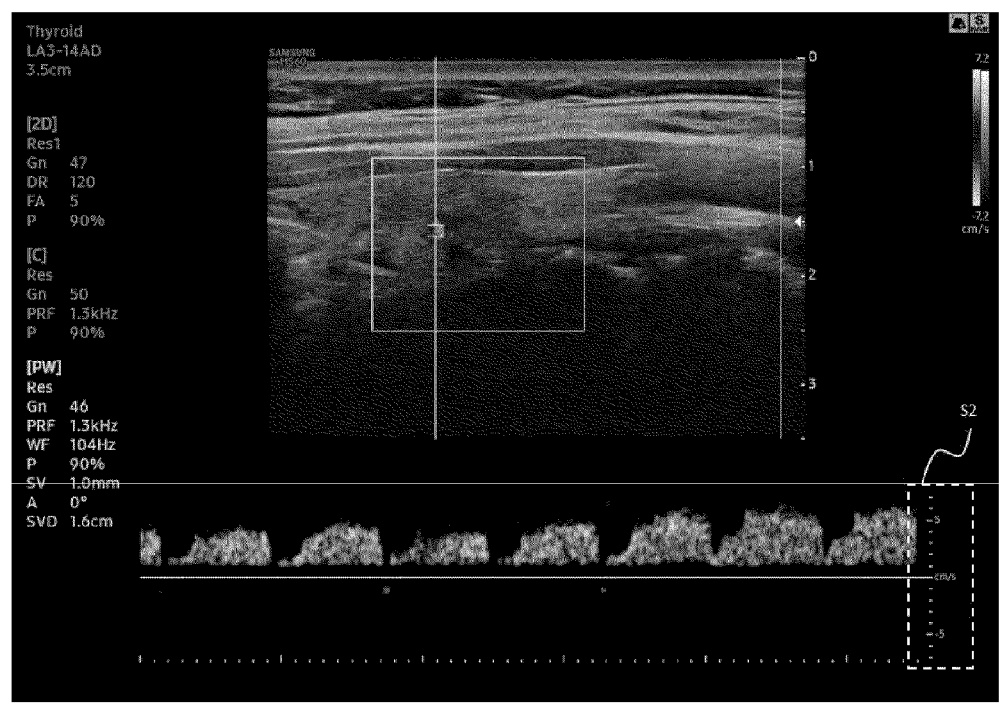

ULTRASOUND DIAGNOSIS APPARATUS FOR CONTROLLING VOLUME OF DOPPLER SOUND AND METHOD OF CONTROLLING THE SAME

CROSS-REFERENCE TO RELATED APPLICATION

This application is based on and claims priority under 35 U.S.C. § 119 to Korean Patent Application No. 2019-0088921, filed on Jul. 23, 2019, in the Korean Intellectual Property Office, the disclosure of which is incorporated herein by reference.

BACKGROUND

1. Field

The disclosure relates to an ultrasound diagnosis apparatus for acquiring an internal image of a target object and Doppler sound using ultrasound, and a method of controlling the same.

2. Description of the Related Art

An ultrasound diagnosis apparatus is designed to irradiate an ultrasound signal generated from a transducer of a probe to a target object and receive information about a signal reflected from the target object to acquire at least one image of an internal part (e.g., a soft tissue or blood flow) of a target object.

An ultrasound system provides Doppler sound together with a Doppler mode image, which represents the velocity of a moving target object as an image using the Doppler effect.

Meanwhile, in the Doppler mode image, the volume of the Doppler sound is determined by the velocity and magnitude of a blood flow of the target object magnitude.

For example, during fetal ultrasound diagnosis, a user checks various blood vessels, such as 'Fetal middle cerebral arterial (MCA)', 'Fetal ductus venous', and 'umbilical cord', and since the Doppler image has a spectrum, the magnitude of which varies depending on the vessel magnitude and the blood flow velocity, and the volume of the Doppler sound dependent on the magnitude of the spectrum varies depending on which part is diagnosed. Accordingly, when the Doppler sound is louder or smaller than required during ultrasound diagnosis, there is an inconvenience that the user needs to manually manipulate the volume separately.

SUMMARY

Therefore, it is an object of the disclosure to provide an ultrasound diagnosis apparatus capable of outputting an optimal volume value of Doppler sound without a user needing to manually manipulate the volume of Doppler sound, and a method of controlling the same.

Additional aspects of the disclosure will be set forth in part in the description which follows and, in part, will be obvious from the description, or may be learned by practice of the disclosure.

In accordance with one aspect of the disclosure, there is provided an ultrasound diagnosis apparatus including: an image processor configured to generates an ultrasound image on the basis of an ultrasound signal; an image outputter configured to display the ultrasound image generated by the image processor on the basis of a plurality of parameters; a sound outputter configured to output Doppler sound of the ultrasound image; and a controller configured to control a volume of the Doppler sound on the basis of at least one of the plurality of parameters.

The ultrasound diagnosis apparatus may further include a storage configured to store a first Doppler gain of an ultrasound signal, wherein the controller may compare the stored first Doppler gain with a second Doppler gain of an ultrasound signal corresponding to the ultrasound image generated in real time by the image processor, and in response to the first Doppler gain being larger than the second Doppler gain, increase the volume of the Doppler sound, and in response to the first Doppler gain being smaller than the second Doppler gain, decrease the volume of the Doppler sound.

The ultrasound diagnosis apparatus may further include an inputter configured to receive a command related to changing the at least one of the plurality of parameters.

The controller may detect a command related to changing a sample volume of pulsed wave (PW) Doppler among the plurality of parameters, and in response to the sample volume being reduced, increase the volume of the Doppler sound, and in response to the sample volume being enlarged, decrease the volume of the Doppler sound.

The controller may detect a command related to changing a gain of pulsed wave (PW) Doppler among the plurality of parameters, and in response to the gain of the PW Doppler being increased, increase the volume of the Doppler sound, and in response to the gain of the PW Doppler being decreased, decrease the volume of the Doppler sound.

The controller may control the volume of the Doppler sound on the basis of at least one of a gain of pulsed wave (PW) Doppler or a gain of continuous wave (CW).

The image outputter may output a spectrum corresponding to the ultrasound image, and the controller may detect a command related to changing a scale of the spectrum among the plurality of parameters, and in response to the scale being decreased, increase the volume of the Doppler sound, and in response to the scale being increased, decrease the volume of the Doppler sound.

The spectrum may include at least one of a spectrum of pulsed wave (PW) Doppler or a spectrum of continuous wave (CW).

The controller may detect a command related to automatically resetting the at least one of the plurality of parameters, and in response to at least one of a scale or a Doppler gain being changed among the plurality of parameters, control the volume of the Doppler sound on the basis of the changed at least one of the scale or the Doppler gain.

In accordance with another aspect of the disclosure, there is provided a method of controlling an ultrasound diagnosis apparatus, the method including: generating an ultrasound image on the basis of an ultrasound signal; displaying the ultrasound image generated on the basis of a plurality of parameters; controlling a volume of Doppler sound of the ultrasound image on the basis of at least one of the plurality of parameters; and outputting the Doppler sound of the ultrasound image.

The controlling of the volume of the Doppler sound may include: storing a first Doppler gain of an ultrasound signal; comparing the stored first Doppler gain with a second Doppler gain of an ultrasound signal corresponding to the ultrasound image generated in real time; and in response to the first Doppler gain being larger than the second Doppler gain, increasing the volume of the Doppler sound; and in response to the first Doppler gain being smaller than the second Doppler gain, decreasing the volume of the Doppler sound.

The method may further include receiving a command related to changing the at least one of the plurality of parameters.

The controlling of the volume of the Doppler sound may include: detecting a command related to changing a sample volume of pulsed wave (PW) Doppler among the plurality of parameters; increasing, in response to the sample volume being reduced, the volume of the Doppler sound, and decreasing, in response to the sample volume being enlarged, the volume of the Doppler sound.

The controlling of the volume of the Doppler sound may include: detecting a command related to changing a gain of pulsed wave (PW) Doppler among the plurality of parameters; increasing, in response to the gain of the PW Doppler being increased, increasing the volume of the Doppler sound; and decreasing, in response to the gain of the PW Doppler being decreased, the volume of the Doppler sound.

The controlling of the volume of the Doppler sound may include controlling the volume of the Doppler sound on the basis of at least one of a gain of pulsed wave (PW) Doppler or a gain of continuous wave (CW).

The displaying of the generated ultrasound image on the basis of the plurality of parameters may include outputting a spectrum corresponding to the ultrasound image, and the controlling of the volume of the Doppler sound may include: detecting a command related to changing a scale of the spectrum among the plurality of parameters, and in response to the scale being decreased, increasing the volume of the Doppler sound, and in response to the scale being increased, decreasing the volume of the Doppler sound.

The spectrum may include at least one of a spectrum of pulsed wave (PW) Doppler or a spectrum of continuous wave (CW).

The controlling of the volume of the Doppler sound may include: detecting a command related to automatically resetting the at least one of the plurality of parameters; and in response to at least one of a scale or a Doppler gain being changed among the plurality of parameters, controlling the volume of the Doppler sound on the basis of the changed at least one of the scale or the Doppler gain.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 1 is an external view illustrating an ultrasound diagnosis apparatus according to an embodiment;

FIG. 2 is a control block diagram illustrating an ultrasound diagnosis apparatus according to an embodiment;

FIG. 3 is a flowchart showing a method of controlling an ultrasound diagnosis apparatus according to an embodiment;

FIG. 4 is a detailed flowchart of the method of controlling the ultrasound diagnosis apparatus shown in FIG. 3;

FIG. 5 is a detailed flowchart of the method of controlling the ultrasound diagnosis apparatus shown in FIG. 3;

FIG. 6 is a view illustrating an ultrasound image referred to FIG. 5;

FIG. 7 is a view illustrating an ultrasound image referred to FIG. 5;

FIG. 8 is a detailed flowchart showing the method of controlling the ultrasound diagnosis apparatus shown in FIG. 3;

FIG. 9 is a view illustrating an ultrasound image referred to FIG. 8;

FIG. 10 is a view illustrating an ultrasound image referred to FIG. 8;

FIG. 11 is a detailed flowchart showing the method of controlling the ultrasound diagnosis apparatus shown in FIG. 3;

FIG. 12 is a view illustrating an ultrasound image referred to FIG. 11; and

FIG. 13 is a view illustrating an ultrasound image referred to FIG. 11.

DETAILED DESCRIPTION

Hereinafter, embodiments of the disclosure will be described in detail with reference to the accompanying drawings. Advantages and features of the disclosure, and methods of achieving the same will be clearly understood with reference to the accompanying drawings and the following detailed embodiments. However, the inventive concept is not limited to embodiments described herein, but may be implemented in various different forms. Rather, these embodiments are provided so that this disclosure is thorough and complete and fully conveys the inventive concept to those skilled in the art, and the scope of the inventive concept is defined by the appended claims. Like numerals refer to like elements throughout the specification.

Unless otherwise defined, all terms including technical and scientific terms used herein have the same meaning as commonly understood by one of ordinary skill in the art to which the disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. The terminology used herein is for the purpose of describing particular embodiments only and is not intended to be limiting of the disclosure. As used herein, the singular forms "a," "an," and "the" are intended to include the plural forms as well, unless the context clearly indicates otherwise.

It will be further understood that the terms "comprises," "comprising," "includes," and/or "including," when used herein, specify the presence of stated features, integers, steps, operations, elements, and/or components but do not preclude the presence or addition of one or more other features, integers, steps, operations, elements, components, and/or groups thereof.

In the following specification, a "target object" may include a human or an animal, or a part of a human or animal. For example, the target object may include organs, such as liver, heart, uterus, brain, breast, and abdomen, or blood vessels. In addition, in the specification, a "user" may be a doctor, a nurse, a clinical pathologist, a medical imaging expert, or the like, and may be a technician who repairs a medical device, but is not limited thereto.

An "ultrasound image" used throughout the specification refers to an image of a target object acquired using ultrasound, and further refers to an image of a target object acquired using an X-ray diagnosis device, a computerized tomography (CT) scanner, a magnetic resonance image (MRI) device, and nuclear medicine. In addition, technology of an ultrasound diagnosis apparatus and a method of controlling the same according to embodiments may be applied to various diagnosis apparatuses, such as an X-ray imaging apparatus, an X-ray fluoroscopy apparatus, a CT scanner, a magnetic resonance imaging apparatus (MRI), a positron emission tomography apparatus, and an ultrasound diagnosis apparatus. Although embodiments are described in relation to an ultrasound diagnosis apparatus by way of example, but the disclosure is not limited thereto.

In the specification, unless explicitly described to the contrary, the word "include" and variations such as "includes" or "including" will be understood to imply the inclusion of stated elements but not the exclusion of any other elements. In addition, a term such as "~ unit" and "module" described in the specification refers to a unit that processes at least one function or operation, which may be implemented in hardware or software, or as a combination of hardware and software.

FIG. 1 is an external view illustrating an ultrasound diagnosis apparatus according to an embodiment.

Referring to FIG. 1, an ultrasound diagnosis apparatus 1 includes a main body 100, an inputter 150 connected to the main body 100, a display panel 160, a sub-display panel 161, and an ultrasound probe P.

A plurality of casters (not shown) for mobility of the ultrasound diagnosis apparatus 1 may be provided in a lower portion of the main body 100 of the ultrasound diagnosis apparatus 1. The plurality of casters may fix the ultrasound diagnosis apparatus 1 in a specific place or move the ultrasound diagnosis apparatus 1 in a specific direction. Such an ultrasound diagnosis apparatus is referred to as a cart-type ultrasound diagnosis apparatus.

Alternatively, unlike FIG. 1, the ultrasound diagnosis apparatus 1 may be a portable ultrasound diagnosis apparatus that may be carried for a long distance movement. In this case, the portable ultrasound diagnosis apparatus may not include a caster. Examples of the portable ultrasound diagnosis apparatus may include a picture archiving and communication system (PACS) viewer, a smart phone, a laptop computer, a personal digital assistant (PDA), a tablet personal computer (a tablet PC), and the like, but are not limited thereto.

The ultrasound probe P is a part that comes in contact with the body surface of a target object and transmits/receives ultrasound to the target object. In detail, the ultrasound probe P may generate ultrasound waves according to an input pulse and transmit the generated ultrasound waves into a target object, and receive echo ultrasound waves reflected from a specific portion inside the target object.

The main body 100 may transmit an ultrasound signal to the ultrasound probe P, receive an echo ultrasound signal from the ultrasound probe P, and generate an ultrasound image on the basis of the received echo ultrasound signal.

The generated ultrasound image may be provided to a user through the display panel 160. The user may diagnose the target object, that is, a patient, by visually checking the ultrasound image of the internal state of the target object provided through the display panel 160.

The display panel 160 may also display various user interfaces (UIs) related to control of the ultrasound diagnosis apparatus 1. The user may check the UI provided through the display panel 160 and input a control command for the ultrasound diagnosis apparatus 1 or a component of the ultrasound diagnosis apparatus 1 through the inputter 150.

In addition, the display panel 160 may display an ultrasound image obtained during an ultrasound diagnosis process. The display panel 160 may be implemented as one of known technologies, such as a cathode ray tube (CRT), a liquid crystal display (LCD), and the like, and may provide not only a two dimensional (2D) image but also a three-dimensional (3D) image.

The user may touch the display panel 160 not only to input a control command for the ultrasound diagnosis apparatus 1 and but also to input a touch command related to setting a region of interest (ROI), in which the user desires to perform observation and diagnosis.

Similar to the display panel 160, the sub-display panel 161 may display various UIs related to control of the ultrasound diagnosis apparatus 1, and the user may check the UI provided through the sub-display panel 161 and input a control command for the ultrasound diagnosis apparatus or a component of the ultrasound diagnosis apparatus through the inputter 150 or a touch screen of the sub-display panel 161.

In addition, the sub-display panel 161 may display ultrasound images obtained in the ultrasound diagnosis process, and the user may touch the sub-display panel 161 to thereby input a control command related to the ultrasound diagnosis apparatus 1 or a command related to setting a ROI in an ultrasound image by. The sub-display panel 161 may include a touch panel capable of receiving a touch input by a user, and the touch panel may be implemented using a liquid crystal display (LCD) panel, a light emitting diode (LED) panel, and an Organic Light Emitting Diode (OLED) panel.

The inputter 150 is a part through which a command related to operation of the ultrasound diagnosis apparatus 1 may be input. The user may input a command related to starting diagnosis, selecting a diagnosis site, selecting a diagnosis type, and selecting a mode for a finally output ultrasound image through the inputter 150.

In addition, the user may input a command related to setting an ROI in an ultrasound image displayed on the display panel 160 or the sub-display panel 161 through the inputter 150. In one embodiment, the inputter 150 may be positioned on an upper portion of the main body 100 as shown in FIG. 1. In this case, the inputter 150 may include at least one of a switch, a key, a wheel, a joystick, a trackball, and a knob.

The ultrasound probe P may be connected to one end of a cable 130 and the other end of the cable 130 may be connected to a male connector 140. The male connector 140 connected to the other end of the cable 130 may be physically coupled to a female connector 145 of the main body 100.

One ultrasound probe P may be connected to one main body 100 according to the above-described method, or a plurality of ultrasound probes P may be connected to one main body 100 in a similar manner. To this end, a plurality of female connectors may be installed on the main body 100. In FIG. 1, a case in which two ultrasound probes 200 are connected to one main body 100 is illustrated.

Alternatively, unlike FIG. 1, the ultrasound probe P may be wirelessly connected to the main body 100. In this case, the ultrasound probe P may wirelessly transmit an echo ultrasound signal corresponding to echo ultrasound received from the target object to the main body 100.

The ultrasound probe P may come in contact with the body surface of the target object and transmit/receive ultrasound to/from the target object. In detail, the ultrasound probe P serves to irradiate ultrasound into the target object according to an ultrasound signal, which is an electrical signal provided from the main body 100, collect echo ultrasound reflected from a specific area inside the target object, and transmit an echo ultrasound signal corresponding to the collected echo ultrasound to the main body 100.

FIG. 2 is a control block diagram illustrating an ultrasound diagnosis apparatus according to an embodiment.

Referring to FIG. 2, the ultrasound diagnosis apparatus 1 according to the embodiment includes an ultrasound probe P, an image processor 10, a controller 50, an inputter 60, an outputter 70, and a storage 80.

As described above, the ultrasound probe P includes a plurality of transducer elements to perform conversion between ultrasound signals and electrical signals. The transducer element transmits an ultrasound signal to a target object, receives an ultrasound echo signal reflected from the target object, and generates a reception signal.

The ultrasound probe P transmits an ultrasound signal to the target object by transmitting a ultrasound beam collected by appropriately delaying the times taken for pulses to be input to the respective the transducer elements along a transmission scan line. Ultrasound echo signals reflected from the target object are input to the respective transducer elements at different reception times, and the respective transducer element output the input ultrasound echo signals.

The beamformer (not shown) may, when the ultrasound probe P transmits ultrasound waves, focus the ultrasound waves to a specific position by adjusting the driving timing of each vibrator of the ultrasound probe P, and when a reception signal is transmitted from the ultrasound probe P, convert the reception signal (an analog signal) into a digital signal. In addition, the beamformer may perform reception and collection on the digital signal in consideration of the position of the transducer elements and the focus point, to generate a receive focused signal.

The image processor 10 generates an ultrasound image by performing an envelope detection process based on the ultrasound signal focused by the beam former to detect the magnitude of the ultrasound signal.

The ultrasound diagnosis apparatus 1 according to the disclosure may generate various types of ultrasound images according to a method of displaying an image, that is, a mode. Various ultrasound images are generated by the image processor 10.

The image processor 10 generates various images based on ultrasound signals received according to modes.

For example, the image processor 10 may display an image in an amplitude mode (A-mode), a motion mode (M-mode), and a brightness mode (B-mode). In particular, the brightness mode (B-mode) is a method of generating an image of a reflected ultrasound signal in brightness of a dot. The brightness of each point is determined in proportion to the amplitude of the reflected ultrasound signal, and provides a brightness level of 256 or more. In addition, the brightness mode (B-mode) may be applied to a color mode in which an image represented in brightness is colored and generated.

Further, the image processor 10 generates a Doppler flow image based on the Doppler effect.

Doppler imaging may display an ultrasound signal at a specific point of a target object as a graph, and may express a variation of flow velocity of a designated area in a B-mode image as a color.

In detail, Doppler imaging may be implemented by various Doppler modes. The Doppler modes may include a color Doppler mode, a power Doppler mode, a Pulsed Wave (PW) Doppler mode, and a Continuous Wave (CW) Doppler mode.

The color Doppler mode visualizes a blood flow pattern of a ROI in an ultrasound image in color, allowing a user to identify the presence and direction of blood flow. For example, blood flow moving toward the ultrasound probe P may be displayed in red, and blood flow moving away from the ultrasound probe P may be displayed in blue.

The Power Doppler mode may record reflected Doppler energy to detect small blood vessels and slow blood flow.

In addition, the PW Doppler mode and the CW Doppler mode are methods of displaying the blood flow velocity at a specific position by time. In detail, in the PW Doppler mode, when a user sets a sample volume for a specific position, the velocity and amount of blood flow at the specific position may be expressed through a spectrum. The PW Doppler mode intermittently transmits and receives ultrasound signals, and the CW Doppler mode continuously transmits and receives ultrasound signals are. The CW Doppler mode displays the velocity of blood flow for the entire CW line (the path of the ultrasound signal) by time. In this case, the PW Doppler mode has aliasing at a high blood flow velocity, causing difficulty in accurately recording a high-speed signal, so that the PW Doppler mode is used complementarily with the CW Doppler mode.

The inputter 60 receives an input command related to the operation of the ultrasound diagnosis apparatus 1 according to the disclosure, converts the received input command into an electrical signal, and transmits the electrical signal to the controller 50.

In detail, the inputter 60 receives a command related to starting an operation of the ultrasound diagnosis apparatus 60 and various operation commands related to changing a generated image. For example, the inputter 60 may receive a command related to executing a power Doppler mode, a command related to executing a color Doppler mode, a command related to executing a PW Doppler mode, and a command related to executing a CW Doppler mode. In addition, the inputter 60 may receive a command related to inputting or changing various parameters in each mode.

The inputter 60 may be implemented in hardware, including a keyboard, trackball, mouse, and touch panel provided in a general ultrasound diagnosis apparatus. When a display 71 shown in FIG. 1 is implemented as a touch screen, the touch screen may perform both the functions of display and inputter.

The display 70 performs an interaction between the ultrasound imaging apparatus 100 and a user.

In detail, the display 70 includes the display panel 160 and the sub-display panel 161 as shown in FIG. 1, and visually provides a user with a generated ultrasound image and various user interfaces.

The sound outputter 90 may output a warning sound and various audible sounds related to an operation to a user through a speaker. Further, the sound outputter 90 may output Doppler sound obtained by converting a spectrum of a Doppler signal generated in a PW Doppler mode or a CW Doppler mode into an audio signal.

The controller 50 refers to a processor that performs the overall operation of the ultrasound diagnosis apparatus 1 according to the disclosure.

In detail, the controller 50 controls the image processor 10 to generate an ultrasound image on the basis of the ultrasound signal transmitted by the ultrasound probe P.

The controller 50 controls the image processor 10 to perform Doppler processing on the basis of based on received ultrasound signal and accumulated data, and to express the blood flow velocity as a spectrum.

Meanwhile, the controller 50 may include a memory (not shown) for storing data regarding various algorithm for controlling the operations of the components of the ultrasound diagnosis apparatus 1 according to the disclosure or a program that represents the algorithm, and a processor (not shown) that performs the above described operations using the data stored in the memory. In this case, the memory and the processor may be implemented as separate chips. Alternatively, the memory and the processor may be implemented as a single chip.

The storage 80 refers to a storage medium that stores various types of data related to operations processed by the controller 50.

The storage 80 according to an example stores data accumulated based on an ultrasound image generated by the image processor 10 or a received ultrasound signal, and provides the stored data during processing operation of the controller 50.

The storage 80 may, when the ultrasound diagnosis apparatus 1 first outputs Doppler sound, store a spectral gain and a basic volume of Doppler sound corresponding to the spectral gain. In addition, when the user changes the volume of the Doppler sound, the storage 80 may store the changed volume of the Doppler sound as a basic volume.

The storage 130 may be implemented in hardware, including a nonvolatile memory device, such as a cache, a read only memory (ROM), a programmable ROM (PROM), an erasable programmable ROM (EPROM), an electrically erasable programmable ROM (EEPROM), and a flash memory, a volatile memory device, such as a random access memory (RAM), or other storage media, such as a hard disk drive (HDD), a CD-ROM, and the like, but the implementation of the storage 80 is not limited thereto. The storage 80 may be a memory implemented as a chip separated from the processor, which has been described above in connection with the controller 50, or may be implemented as a single chip integrated with the processor.

At least one component may be added or omitted to correspond to the performances of the components of the ultrasound diagnosis apparatus 1 shown in FIG. 2. In addition, the mutual positions of the components may be changed to correspond to the performance or structure of the system.

Some of the components shown in FIG. 2 may refer to a software component and/or a hardware component, such as a Field Programmable Gate Array (FPGA) and an Application Specific Integrated Circuit (ASIC).

FIG. 3 is a flowchart showing a method of controlling an ultrasound diagnosis apparatus according to an embodiment.

The ultrasound diagnosis apparatus 1 generates an ultrasound image on the basis of ultrasound signals (301). In this case, the image processor 10 may generate various images using ultrasound signals received according to a specific mode. For example, the image processor 10 generates an ultrasound image using ultrasound signals received according to at least one of a color Doppler mode, a power Doppler mode, a PW Doppler mode, or a CW Doppler mode.

The ultrasound diagnosis apparatus 1 may display the ultrasound image generated by the image processor 10 on the basis of a plurality of parameters (302). In detail, the display 70 may generate an ultrasound image on the basis of a plurality of parameters, and when the ultrasound image is generated in a PW Doppler mode or CW Doppler mode, may display a spectrum corresponding to the ultrasound signal together with the ultrasound image.

Here, the plurality of parameters may include gain information (Gain), pulse repetition frequency (PRF), sample volume (SV), dynamic range (DR), and time gain compensation (TGC), a baseline, and a scale of the ultrasound image.

The ultrasound diagnosis apparatus 1 may output the ultrasound image through the display 70 on the basis of the previously stored plurality of parameters, and may output a spectrum in a PW Doppler mode or CW Doppler mode together with the ultrasound image. In addition, the ultrasound diagnosis apparatus 1 may, in response to a change command for changing at least one of the plurality of parameters, control the output of the spectrum to be changed.

The ultrasound diagnosis apparatus 1 may control the volume of the Doppler sound on the basis of at least one of the plurality of parameters (303). For example, the ultrasound diagnosis apparatus 1 may control the volume of the Doppler sound so that the volume of the Doppler sound is proportional to the currently set gain value, on the basis of gain information of the ultrasound image. In addition, the ultrasound diagnosis apparatus 1 may, in response to a change command for at least one of the plurality of parameters, control output of the spectrum to be changed, and control the volume of the Doppler sound according to a change of the spectrum. Details thereof will be described in detail with reference to FIGS. 4 to 16.

Finally, the ultrasound diagnosis apparatus 1 outputs Doppler sound on the basis of the magnitude of volume of Doppler sound changed in operation 303 (304). Accordingly, the user may listen to the Doppler sound suitable for ultrasound diagnosis without manually adjusting the volume of the Doppler sound.

FIG. 4 is a detailed flowchart of the method of controlling the ultrasound diagnosis apparatus shown in FIG. 3.

According to an embodiment of the disclosure, the ultrasound diagnosis apparatus 1 may estimate the magnitude of a spectrum to be output, and output Doppler sound having a volume suitable for the estimated magnitude of spectrum.

The ultrasound diagnosis apparatus 1 may execute one of a color Doppler mode and a power Doppler mode before a PW Doppler mode is executed (401).

In order to estimate the magnitude of spectrum, which will be reflected in the volume of Doppler sound, the ultrasound diagnosis apparatus 1 acquires a first Doppler gain corresponding to a predetermined region and stored in advance (402). In detail, the controller 50 may store Doppler gain in the storage 80 on the basis of frame information of power Doppler. In addition, in the case of color Doppler, the controller 50 may store color Doppler gains in the storage 80 on the basis of a position of the ROI.

The ultrasound diagnosis apparatus 1 acquires a second Doppler gain corresponding to the predetermined region from a currently output ultrasound image (403). In this case, the second Doppler gain refers to gain information that may be proportionally reflected in a spectrum of PW Doppler mode or a spectrum of CW Doppler mode that is currently to be output.

The first Doppler gain and the second Doppler gain may serve as a reference for controlling the Doppler sound according to the magnitude of a ultrasound signal without a user inputting a change command for a parameter. For example, the ultrasound diagnosis apparatus 1 may have the first Doppler gain when capturing a first region of the target object, and may have the second Doppler gain when capturing a second region of the target object.

In addition, unlike the embodiment shown in FIG. 4, the ultrasound diagnosis apparatus 1 may control the volume of the Doppler sound on the basis of on a user gain changed by a user among the plurality of parameters.

The ultrasound diagnosis apparatus 1 compares the first Doppler gain with the second Doppler gain (404). The volume of the Doppler sound to be output may serve as reference for comparing the last measured power Doppler gain or color Doppler gain, and assigning a compensation value according to the comparison result.

When the current power Doppler gain or color Doppler gain is large, it may be predicted that the blood flow velocity and the magnitude of the spectrum according to the blood flow velocity are great. Therefore, the volume of the Doppler sound is expected to be output more than needed.

Accordingly, when the first Doppler gain is greater than the second Doppler gain (405), the ultrasound diagnosis apparatus 1 controls the volume of the Doppler sound to increase (406), and when the first Doppler gain is less than the second Doppler gain (405), controls the volume of the Doppler sound to decrease (407).

The embodiment of FIG. 4 has been described in relation to a power Doppler mode as an example. However, the embodiment shown in FIG. 4 may control the volume of the Doppler sound not only based on the power Doppler gain stored in the power Doppler mode but also based on a PW Doppler gain, a CW Doppler gain, or a color Doppler gain.

Meanwhile the ultrasound diagnosis apparatus 1 according to the disclosure may not only control the volume of the Doppler sound based on the stored parameter but also may control the volume of the Doppler sound based on a change of a user parameter. For example, before executing the PW Doppler mode, when the size of the blood vessel is large, the user may change the sample volume. A control method based on a change of user parameter will be described in detail with reference to FIGS. 5 to 7.

FIG. 5 is a detailed flowchart of the method of controlling the ultrasound diagnosis apparatus shown in FIG. 3. FIG. 6 is a view illustrating an ultrasound image referred to FIG. 5. FIG. 7 is a view illustrating an ultrasound image referred to FIG. 5.

The ultrasound diagnosis apparatus 1 receives a parameter change command from a user through the inputter 60 (501). In this case, the parameter change command may be a command related to changing the size of the sample volume. Referring to FIGS. 6 and 7, it can be seen that the size of the sample volume P1 has been enlarged from 2.5 mm to 3.5 mm by a change command input by a user.

The ultrasound diagnosis apparatus 1 detects a command related to changing the sample volume of PW Doppler (502), and checks whether the sample volume has been reduced (503).

For example, as for an enlarged sample volume, it may be estimated that the size of the blood vessel is large, and when the size of the blood vessel is large, it may be estimated that the intensity and velocity of blood flow are great. Therefore, it may be expected that the output PW Doppler gain and the volume of Doppler sound set in advance are relatively large, and when a relatively large volume of Doppler sound is output, the user is expected to decrease the volume. However, according to the embodiment, the volume of the Doppler sound may be automatically controlled on the basis of the above described estimation result without a need for the user to manually adjust the volume of Doppler sound.

In detail, in response to the sample volume being reduced, the ultrasound diagnosis apparatus 1 increases the volume of the Doppler sound (504), and in response to the sample volume being enlarged, the ultrasound diagnosis apparatus 1 may decrease the volume of the Doppler sound (505).

Meanwhile, the user may change a gain value during execution of the PW Doppler mode. Increasing a gain value by the user represents that the blood flow velocity or the blood flow intensity of the target object is low, and thus the volume of the Doppler sound is expected to be low. An embodiment for removing such a limitation will be described with reference to FIGS. 8 to 10.

FIG. 8 is a detailed flowchart showing the method of controlling the ultrasound diagnosis apparatus shown in FIG. 3. FIG. 9 is a view illustrating an ultrasound image referred to FIG. 8. FIG. 10 is a view illustrating an ultrasound image referred to FIG. 8.

The ultrasound diagnosis apparatus 1 receives a parameter change command from a user through the inputter 60 (801). In this case, the parameter change command may be a command related to changing the PW Doppler gain. Referring to FIGS. 9 and 10, it can be seen that a user has changed the PW Doppler gain P2 from 44 to 54 in order to compensate for the weak signal value of a spectrum S of PW Doppler mode. In this case, a small PW Doppler gain represents that the intensity of blood flow is weak, and it may be expected that the volume of the Doppler sound to be output is also small.

The ultrasound diagnosis apparatus 1 detects a command for changing the PW Doppler gain (802) and checks whether the PW Doppler gain has been increased (803). Although the embodiment of FIG. 8 has been described in relation to PW Doppler as an example, the embodiment may also apply to CW Doppler.

For example, increasing a PW Doppler gain by the user is provided to compensate for the spectrum and the Doppler sound on the weak blood flow intensity. According to the embodiment, even in the case of weak blood flow, the volume of the Doppler sound may be automatically controlled without the need for the user to manually adjust the volume level.

In detail, the ultrasound diagnosis apparatus 1 may, in response to the PW Doppler gain being increased, increase the volume of the Doppler sound (804), and in response to the PW Doppler gain being decreased, decrease the volume of the Doppler sound (505).

Next, an embodiment of controlling the volume of the Doppler sound when the user adjusts the scale during execution of the PW Doppler mode will be described.

FIG. 11 is a detailed flowchart showing the method of controlling the ultrasound diagnosis apparatus shown in FIG. 3. FIG. 12 is a view illustrating an ultrasound image referred to FIG. 11. FIG. 13 is a view illustrating an ultrasound image referred to FIG. 11.

The ultrasound diagnosis apparatus 1 receives a parameter change command from a user through the inputter 60 (1101). In this case, the parameter change command may be a command related to changing the scale of a spectrum during execution of the PW Doppler mode.

Referring to FIG. 12, the scale may be in a range of −10 cm/s to +10 cm/s. Such a range of scale represents that the blood flow velocity of the target object is relatively low, and the user needs to adjust the range of the spectrum scale to be small to perform precise observation. Referring to FIG. 13, it can be seen that the scale is changed to have a range of −5 cm/s to +5 cm/s according to a scale change command input by a user.

Referring to the spectral scale shown in FIG. 12, the volume of the Doppler sound may be estimated to be smaller than the volume of the Doppler sound desired by the user. According to the present embodiment, when the scale of a spectrum having a low blood flow velocity is enlarged, the volume of the Doppler sound may be automatically controlled to correspond to the enlargement The ultrasound diagnosis apparatus 1 detects a command related to changing the scale of the spectrum in the PW Doppler mode (1102), and checks whether the scale range of the spectrum is reduced (1103). Although the embodiment of FIG. 11 has been described in relation to a PW Doppler mode as an example, the embodiment may apply to a CW Doppler mode.

In detail, the ultrasound diagnosis apparatus 1 may, when the scale range of the spectrum is reduced, increase the volume of the Doppler sound (1104), and when the scale range of the spectrum is enlarged, decrease the volume of the Doppler sound (1105).

The ultrasound diagnosis apparatus 1 according to the disclosure may automatically reset a plurality of parameters without manually setting parameters to improve user convenience. Here, the plurality of parameters include gain information (Gain), pulse repetition frequency (PRF), sample volume (SV), dynamic range (DR), and time gain compensation (TGC), a baseline, and a scale of the ultrasound image, and optimal parameters may be automatically reset according to a target object to be diagnosed, on the basis of the type of the target object and a past diagnosis history.

The ultrasound diagnosis apparatus 1 according to the embodiment may, in response to detecting a command related to resetting the plurality of parameters by a user, automatically change a setting value of at least one of the plurality of parameters. For example, when at least one of the scale or the Doppler gain is changed according to the resetting, the ultrasound diagnosis apparatus 1 may control the volume of the Doppler sound on the basis of the changed scale and the changed Doppler gain.

Meanwhile, the disclosed embodiments may be embodied in the form of a recording medium storing instructions executable by a computer. The instructions may be stored in the form of program code and, when executed by a processor, may generate a program module to perform the operations of the disclosed embodiments. The recording medium may be embodied as a computer-readable recording medium.

The computer-readable recording medium includes all kinds of recording media in which instructions which may be decoded by a computer are stored, for example, a Read Only Memory (ROM), a Random Access Memory (RAM), a magnetic tape, a magnetic disk, a flash memory, an optical data storage device, and the like.

As is apparent from the above, the volume of Doppler sound is automatically adjusted, so that a user does not need to manually manipulate the volume, thereby providing convenience in ultrasound diagnosis.

Although exemplary embodiments of the present invention have been described for illustrative purposes, those skilled in the art will appreciate that various modifications, additions and substitutions are possible, without departing from the scope and spirit of the disclosure. Therefore, exemplary embodiments of the present invention have not been described for limiting purposes.

What is claimed is:

1. An ultrasound diagnosis apparatus comprising:
an image processor configured to generates an ultrasound image on the basis of an ultrasound signal;
an image outputter configured to display the ultrasound image generated by the image processor on the basis of a plurality of parameters;
a sound outputter configured to output Doppler sound of the ultrasound image;
an inputter configured to receive a command related to changing at least one of the plurality of parameters;
a controller configured to control a volume of the Doppler sound on the basis of the at least one of the plurality of parameters,
a storage configured to store a first Doppler gain of an ultrasound signal,
wherein the controller detects a command related to changing a sample volume of pulsed wave (PW) Doppler among the plurality of parameters, and
wherein the controller compares the stored first Doppler gain with a second Doppler gain of an ultrasound signal corresponding to the ultrasound image generated in real time by the image processor, and in response to the sample volume being reduced and the first Doppler gain being larger than the second Doppler gain, increases the volume of the Doppler sound, and in response to the sample volume being enlarged and the first Doppler gain being smaller than the second Doppler gain, decreases the volume of the Doppler sound.

2. The ultrasound diagnosis apparatus of claim 1, wherein the controller detects a command related to changing a gain of pulsed wave (PW) Doppler among the plurality of parameters, and in response to the gain of the PW Doppler being increased, increases the volume of the Doppler sound, and in response to the gain of the PW Doppler being decreased, decreases the volume of the Doppler sound.

3. The ultrasound diagnosis apparatus of claim 2, wherein the controller controls the volume of the Doppler sound on the basis of at least one of a gain of pulsed wave (PW) Doppler or a gain of continuous wave (CW).

4. The ultrasound diagnosis apparatus of claim 1, wherein the image outputter outputs a spectrum corresponding to the ultrasound image, and
the controller detects a command related to changing a scale of the spectrum among the plurality of parameters, and in response to the scale being decreased, increases the volume of the Doppler sound, and in response to the scale being increased, decreases the volume of the Doppler sound.

5. The ultrasound diagnosis apparatus of claim 4, wherein the spectrum includes at least one of a spectrum of pulsed wave (PW) Doppler or a spectrum of continuous wave (CW).

6. The ultrasound diagnosis apparatus of claim 1, wherein the controller detects a command related to automatically resetting the at least one of the plurality of parameters, and in response to at least one of a scale or a Doppler gain being changed among the plurality of parameters, controls the volume of the Doppler sound on the basis of the changed at least one of the scale or the Doppler gain.

7. A method of controlling an ultrasound diagnosis apparatus, the method comprising:
generating an ultrasound image on the basis of an ultrasound signal; displaying the ultrasound image generated on the basis of a plurality of parameters;
receiving a command related to changing at least one of the plurality of parameters;
controlling a volume of Doppler sound of the ultrasound image on the basis of the at least one of the plurality of parameters; and outputting the Doppler sound of the ultrasound image,
wherein the controlling of the volume of the Doppler sound includes:
detecting a command related to changing a sample volume of pulsed wave (PW) Doppler among the plurality of parameters;
storing a first Doppler gain of an ultrasound signal; and
comparing the stored first Doppler gain with a second Doppler gain of an ultrasound signal corresponding to the ultrasound image generated in real time; and in response to the sample volume being reduced and the first Doppler gain being larger than the second Doppler gain, increasing the volume of the Doppler sound; and in response to the sample volume being enlarged and the first Doppler gain being smaller than the second Doppler gain, decreasing the volume of the Doppler sound.

8. The method of claim 7, wherein the controlling of the volume of the Doppler sound includes:

detecting a command related to changing a gain of pulsed wave (PW) Doppler among the plurality of parameters;

increasing, in response to the gain of the PW Doppler being increased, increasing the volume of the Doppler sound; and decreasing, in response to the gain of the PW Doppler being decreased, the volume of the Doppler sound.

9. The method of claim 8, wherein the controlling of the volume of the Doppler sound includes controlling the volume of the Doppler sound on the basis of at least one of a gain of pulsed wave (PW) Doppler or a gain of continuous wave (CW).

10. The method of claim 7, wherein the displaying of the generated ultrasound image on the basis of the plurality of parameters includes outputting a spectrum corresponding to the ultrasound image, and the controlling of the volume of the Doppler sound includes:

detecting a command related to changing a scale of the spectrum among the plurality of parameters, and in response to the scale being decreased, increasing the volume of the Doppler sound, and in response to the scale being increased, decreasing the volume of the Doppler sound.

11. The method of claim 10, wherein the spectrum includes at least one of a spectrum of pulsed wave (PW) Doppler or a spectrum of continuous wave (CW).

12. The method of claim 7, wherein the controlling of the volume of the Doppler sound includes:

detecting a command related to automatically resetting the at least one of the plurality of parameters; and in response to at least one of a scale or a Doppler gain being changed among the plurality of parameters, controlling the volume of the Doppler sound on the basis of the changed at least one of the scale or the Doppler gain.

* * * * *